US006789897B2

(12) United States Patent
Smith

(10) Patent No.: US 6,789,897 B2
(45) Date of Patent: Sep. 14, 2004

(54) BINOCULAR GLASSES

(76) Inventor: Anita F. Smith, 20258 Woodmont St., Harper Woods, MI (US) 48225

( * ) Notice: Subject to any disclaimer, the term of this patent is extended or adjusted under 35 U.S.C. 154(b) by 0 days.

(21) Appl. No.: 10/320,520

(22) Filed: Dec. 17, 2002

(65) Prior Publication Data

US 2004/0114097 A1 Jun. 17, 2004

(51) Int. Cl.⁷ .................................................. G02C 7/02
(52) U.S. Cl. ........................ 351/159; 351/51; 359/407; D16/306; D16/133
(58) Field of Search ................................ 351/159, 177, 351/178, 41, 51–52, 45–47; 359/407–418; D16/101, 300, 306, 323–324, 330, 334, 133–136

(56) References Cited

U.S. PATENT DOCUMENTS

| | | | |
|---|---|---|---|
| 2,422,661 A | 6/1947 | Ellis | 359/481 |
| 2,437,642 A | 3/1948 | Henroteau | 351/41 |
| 3,741,634 A | 6/1973 | Stoltze | 351/57 |
| 4,429,959 A | 2/1984 | Walters | 351/158 |
| 4,776,686 A | * 10/1988 | Stanley et al. | 351/115 |
| 4,984,879 A | 1/1991 | Plunkett | 359/408 |
| D321,700 S | 11/1991 | Smith | D16/306 |
| 5,485,305 A | 1/1996 | Johnson | 359/407 |
| D375,968 S | 11/1996 | Ushiyama | D16/133 |
| D379,188 S | 5/1997 | Ushiyama | D16/133 |
| D394,442 S | 5/1998 | Ushiyama | D16/133 |
| 5,825,537 A | * 10/1998 | Ushiyama | 359/408 |
| 5,896,184 A | * 4/1999 | Lowe et al. | 351/52 |
| 6,002,517 A | 12/1999 | Elkind | 359/409 |
| 6,172,808 B1 | * 1/2001 | Foreman et al. | 359/481 |
| 2003/0016443 A1 | * 1/2003 | Shin | 359/408 |
| 2003/0112506 A1 | * 6/2003 | Cromer | 359/407 |

\* cited by examiner

Primary Examiner—Jordan M. Schwartz
(74) Attorney, Agent, or Firm—Richard C. Litman

(57) ABSTRACT

Sports theme hands-free binocular glasses having an eyeglass frame, a binocular device, and an ornamental device, where the ornamental device has an overall shape which is substantially the shape of a sports-related device, and where the ornamental device has an opening which allows light to pass through the opening and into the binocular device. The ornamental device may be hollow and adapted to enclose the binocular device, and may comprise a first design element, where the first design element has a first design element shape which is substantially the shape of an attribute of the sports-related device. The sports theme hands-free binocular glasses may be adapted for use as a hands-free device. Also, hands-free binocular glasses having an eyeglass frame, a binocular device, a decorative element and a design element.

19 Claims, 9 Drawing Sheets

BINOCULAR GLASSES

BACKGROUND OF THE INVENTION

1. Field of the Invention

The present invention relates to binocular glasses, and particularly sports theme hands-free binocular glasses or hands-free binocular glasses with decorative and design elements.

2. Description of the Related Art

Observers of an event, in particular sports fans, concert-goers and opera-goers, often use binoculars to observe the event from a distance. Binoculars are typically operated with one or both hands. This is problematic, for example, during a sporting event, since a sports fan cannot simultaneously watch the game through binoculars and perform some other activity that requires the use of hands, such as drinking a beer, eating a hot dog, or using a cellular telephone.

While various hands-free binoculars have been proposed, they are often expensive and not specifically designed with the sports fan, concert-goer or opera-goer in mind. For example, U.S. Pat. No. 2,422,661, issued Jun. 24, 1947 to C. A. Ellis, describes a binocular magnifying lens holder. U.S. Pat. No. 2,437,642, issued Mar. 9, 1948 to F. C. P. Henroteau, describes spectacles for vision correction. U.S. Pat. No. 3,741,634, issued Jun. 26, 1973 to Stoltze, describes binocular spectacles.

Further, U.S. Pat. No. 4,429,959, issued Feb. 7, 1984 to Walters, describes a spectacle mounted hinged monocular or binocular vision aid. U.S. Pat. No. 5,485,305, issued Jan. 16, 1996 to Johnson, describes a lightweight binocular telescope. U.S. Pat. No. 6,002,517, issued Dec. 14, 1999 to Elkind, describes flat, hands-free, convertible Keplerian binoculars.

Also, while some sports theme binoculars have been proposed, they do not solve the above-described problem of requiring the use of hands. For example, U.S. Pat. No. 4,984,879, issued Jan. 15, 1991 to Plunkett, describes a comfortable binocular. U.S. Design Pat. No. 375,968, issued Nov. 26, 1996 to Ushiyama, describes baseball-type binoculars. U.S. Design Pat. No. 379,188, issued May 13, 1997 to Ushiyama, describes soccerball-type binoculars. U.S. Design Pat. No. 394,442, issued May 19, 1998 to Ushiyama, describes basketball-type binoculars.

Finally, while sports theme eyeglasses have been proposed, it does not include a binocular function. U.S. Design Pat. No. 321,700, issued Nov. 19, 1991 to Smith, describes novelty sunglasses with a golf ball-like feature.

None of the above inventions and patents, taken either singularly or in combination, is seen to describe the instant invention as claimed. Thus binocular glasses solving the aforementioned problems is desired.

SUMMARY OF THE INVENTION

The sports theme hands-free binocular glasses of the present invention comprise an eyeglass frame, a binocular device, and an ornamental device. The ornamental device has an overall shape which is substantially the shape of a sports-related device. The ornamental device has an opening which allows light to pass through the opening and into the binocular device. The ornamental device may be hollow and adapted to enclose the binocular device. The ornamental device may comprise a first design element, where the first design element has a first design element shape which is substantially the shape of an attribute of the sports-related device. The sports theme hands-free binocular glasses may be adapted for use as a hands-free device. Also, the present invention is directed to hands-free binocular glasses having an eyeglass frame, a binocular device, a decorative element and a design element.

Accordingly, it is a principal object of the invention to provide sports theme hands-free binocular glasses comprising an eyeglass frame, a binocular device, an ornamental device, and a sports-related design.

It is another object of the invention to provide hands-free sports theme hands-free binocular glasses comprising an eyeglass frame, a binocular device, an ornamental device, and a sports-related design.

It is a further object of the invention to provide hands-free binocular glasses having an eyeglass frame, a binocular device, a decorative element and a design element.

Still another object of the invention is to provide hands-free sports theme hands-free binocular glasses comprising an eyeglass frame, a binocular device, an ornamental device, and a sports-related design element, where the overall shape of the ornamental device is substantially the shape of a sports-related device, where the ornamental device comprises a first design element, and where the first design element has a first design element shape which is substantially the shape of an attribute of the sports-related device.

It is an object of the invention to provide improved elements and arrangements thereof for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
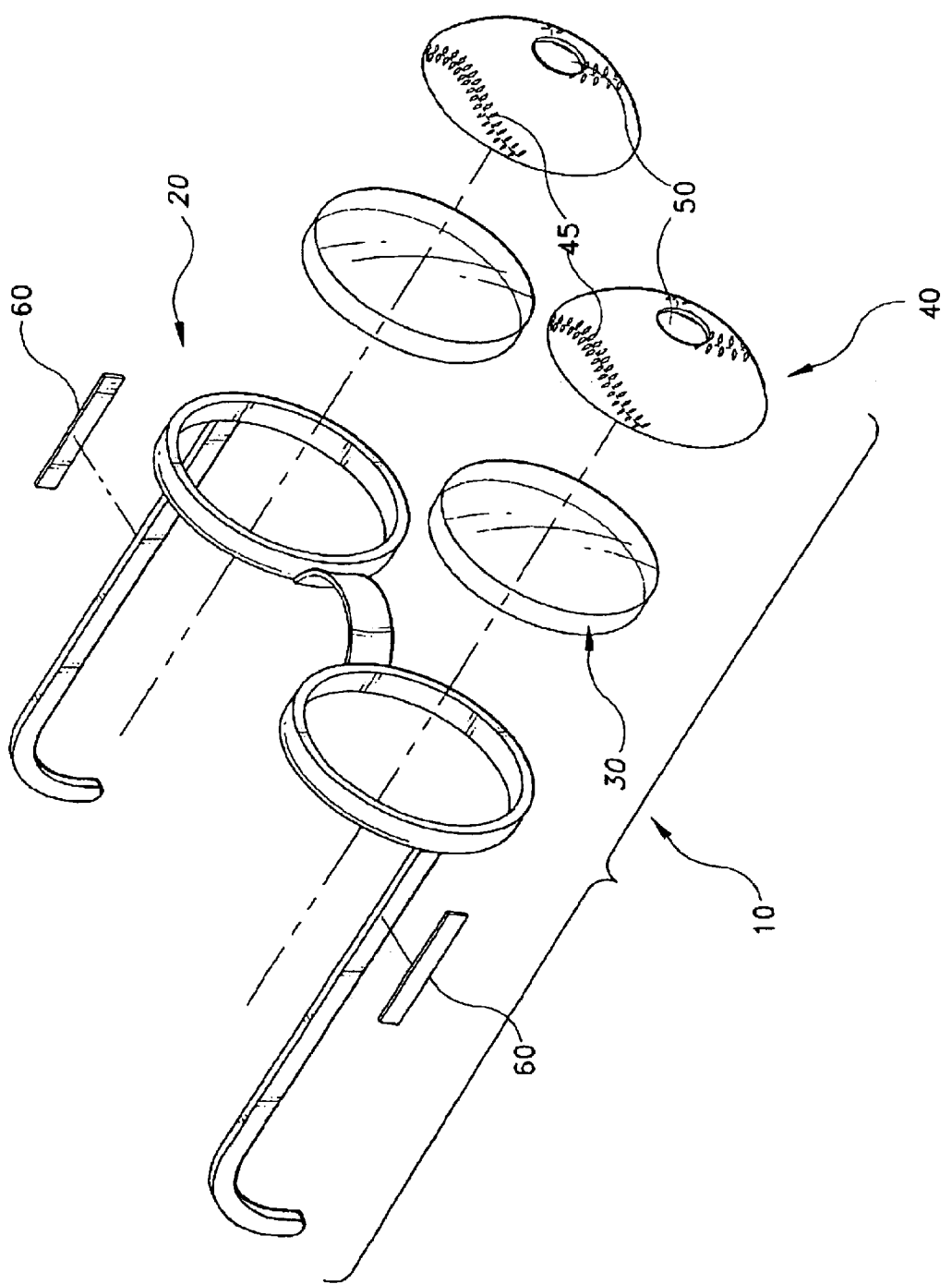
FIG. 1 is an environmental, perspective view of sports theme hands-free binocular glasses according to the present invention with a baseball theme.

The present invention is directed to binocular glasses, designated generally as 10 in the drawings. The binocular glasses 10 may be worn by a wearer in the same manner as regular eyeglasses and may feature a sports-theme as an integral part of the design. The sports theme hands-free binocular glasses 10 are particularly adapted to be adorned with an ornamental device 40 which corresponds with the event, the sport, and/or the team being observed. The sports theme hands-free binocular glasses 10 may be intended for sale as a novelty item at a sporting event.

In a first embodiment, examples of which are shown in FIGS. 1 to 8, sports theme hands-free binocular glasses 10 comprise an eyeglass frame 20, a binocular device 30 adapted for attachment to the eyeglass frame 20, and an ornamental device 40 adapted for attachment to the eyeglass frame 20. The ornamental device 40 has an overall shape which is substantially the shape of a sports-related device. The ornamental device 40 has an opening 50 which allows light to pass through the opening 50 and into the binocular device 30.

Due to the integration of the binocular device 30 with the eyeglass frame 20, a wearer is able to use the sports theme hands-free binocular glasses 10 without the use of hands. For example, a sports fan can watch a game by wearing the sports theme hands-free binocular glasses 10 of the present invention while simultaneously holding a drink or hot dog.

The eyeglass frame 20, the binocular device 30 and the ornamental device 40 may be adapted for attachment using any suitable means and in any suitable manner. For example, the eyeglass frame 20 may be adapted to receive the binocular device 30 and the binocular device 30 may be adapted to receive the ornamental device 40. Alternately, the eyeglass frame 20 may be adapted to receive the ornamental device 40 and the ornamental device 40 may be adapted to receive the binocular device 30. Further, the eyeglass frame 20 may be adapted to receive both the binocular device 30 and the ornamental device 40. In yet another alternate form, the binocular device 30 may protrude through the opening 50 of the ornamental device 40 (not shown), or the binocular device 30 may be enclosed inside the ornamental device 40 (as shown).

The eyeglass frame 20 may be any suitable device for supporting the binocular device 30 and the ornamental device 40 on the head of a wearer. The eyeglass frame 20 may be provided in any suitable shape and size for use by an adult or child wearer. The eyeglass frame 20 may be made of any suitable material, such as metal or plastic.

The binocular device 30 may be any suitable binocular device for magnifying distant objects. In using the term "binocular device," the present inventor means that the binocular device 30 is an optical device designed for use by both eyes simultaneously and has a greater magnification power than conventional corrective eyeglasses. The sports theme hands-free binocular glasses 10 of the present invention may be adapted for sale as a novelty item at sporting events. In such cases, the binocular device 30 may preferably be compact, lightweight and inexpensive.

The binocular device 30 may comprise a pair of devices (as shown) or a single unit (not shown) adapted for attachment to the eyeglass frame 20 or integrated into the ornamental device 40. For example, the binocular device 30 may comprise a pair of compact monolithic lightweight telescopic lenses or the like, which are readily adapted for mounting in the eyeglass frame 20.

Optionally, the binocular device 30 may comprise an objective lens, an ocular lens, or a prism between the objective and ocular lenses. For example, the binocular device 30 may comprise porro prism type binoculars or dach (or roof) prism type binoculars. Also, optionally, the binocular device 30 may comprise either fixed magnification binoculars or zoom type binoculars.

Further, the binocular device 30 may further comprise a focusing knob, a diopter adjustment knob, a permafocus knob, and/or a center barrel focus knob. The knobs may be have an overall shape which is substantially the shape of a sports-related device. For example, for the baseball-themed sports theme hands-free binocular glasses 10 (FIG. 1), the knob could be provided in the shape of a portion of a baseball.

Using, for example, a 10×50 strength binocular device, the sports theme hands-free binocular glasses 10 of the present invention permit a wearer to see objects 100 yards away as if they were only 10 yards away.

As noted above, the ornamental device 40 may comprise any suitable device which allows light to pass through the opening 50 and into the binocular device 30. The ornamental device 40 has an overall shape which is substantially the shape of a sports-related device. The overall shape may be, for example, semispherical, cylindrical, or oblong, as is appropriate to emulate the shape of, for example, a ball, a hockey puck, or a football. A sports-related device may comprise any device used in a sporting event, examples of which are provided in greater detail below. The ornamental device 40 may be made of any suitable material, such as plastic or natural materials.

The opening 50 may be provided in any suitable size and shape. Although the opening 50 illustrated in FIGS. 1 to 8 is relatively small compared to the overall size of the ornamental device 40, the opening 50 may be relatively large compared to the overall size of the ornamental device 40. It is desirable that the size of the opening 50 provide a sufficient field of vision for the sports theme hands-free binocular glasses 10.

In a second embodiment, examples of which are shown in FIGS. 1 to 4 and FIGS. 6 to 8, the sports theme hands-free binocular glasses 10 include all the features of the first embodiment, and the overall shape of the ornamental device 40 is substantially semispherical. The overall shape may be any suitable shape for covering or protecting the binocular device 30 while simultaneously providing a shape which is substantially similar to that of a sports-related device. In order to better accommodate the dimensions of eyeglasses, the substantially semispherical overall shape may be a flattened semispherical shape. A substantially semispherical overall shape is useful in emulating the shape of most sports-related devices.

Figure 5:
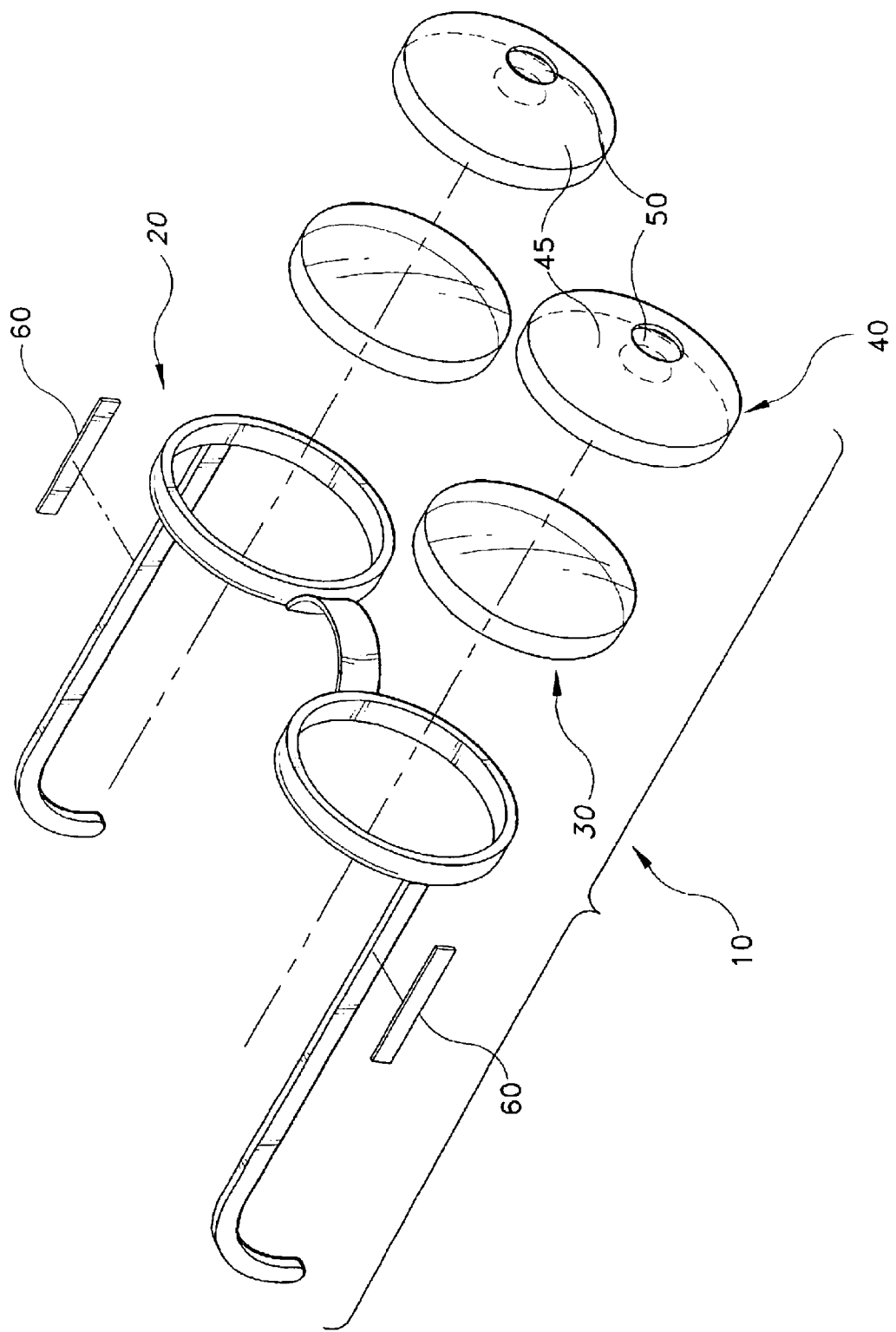
FIG. 5 is an environmental, perspective view of sports theme hands-free binocular glasses according to the present invention with a hockey theme.

In a third embodiment, an example of which is shown in FIG. 5, the sports theme hands-free binocular glasses 10 include all the features of the first embodiment, and the overall shape of the ornamental device 40 is substantially cylindrical. A substantially cylindrical shape is useful in emulating the shape of a sports-related device such as a hockey puck.

In a fourth embodiment, examples of which are shown in FIGS. 1 to 4 and FIGS. 6 to 8, the sports theme hands-free binocular glasses 10 include all the features of the first embodiment, and the ornamental device 40 is hollow and adapted to enclose the binocular device 30. In the fourth embodiment, the ornamental device 40 has the additional advantage of protecting the binocular device 30 from external elements and debris.

In a fifth embodiment, examples of which are shown in FIGS. 1 to 8, the sports theme hands-free binocular glasses 10 include all the features of the first embodiment, and the ornamental device 40 comprises a first design element 45. The first design element 45 may comprise any suitable device in any suitable shape for emulating an element of a sports-related device. The first design element 45 may comprise, for example, a sticker or an applique adapted for attachment to the surface of the ornamental device 40, or a design element integrated or molded into the overall shape of the ornamental device 40. The first design element 45 may comprise, for example, a color scheme for a team, a logo, a name, a number corresponding with a player, etc. Examples of the first design element 45 in the form of a design element integrated or molded into the overall shape of the ornamental device 40 are described in greater detail below.

Figure 6:
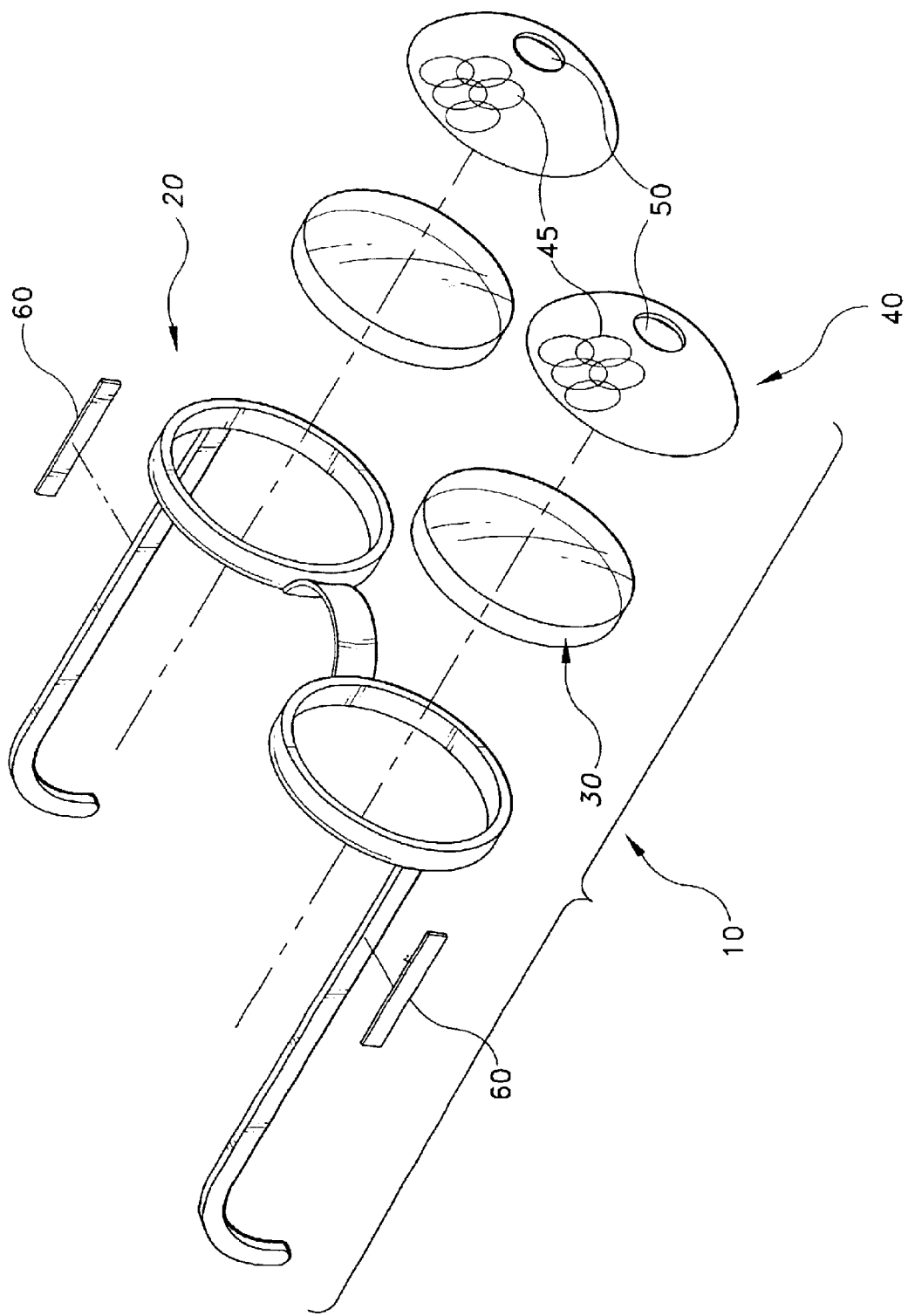
FIG. 6 is an environmental, perspective view of sports theme hands-free binocular glasses according to the present invention with an OLYMPIC theme.

As shown in FIG. 6, the design element 45 may comprise, for example, a sticker or an applique adapted for attachment to the surface of the ornamental device 40, or a design element integrated or molded into the overall shape of the ornamental device 40, where the sticker, applique or design element corresponds with a sporting event, such as the OLYMPICS. The design element 45 may comprise, for example, an integrated or molded element in the shape of the OLYMPIC rings. The second design element 60 may comprise, for example, the name of a host country or city, the name of a particular OLYMPIC event, and/or a symbol representing the event.

In a sixth embodiment, examples of which are shown in FIGS. 1 to 8, the sports theme hands-free binocular glasses 10 include all the features of the fifth embodiment, and the first design element 45 has a first design element shape which is substantially the shape of an attribute of the sports-related device. Examples of the attribute are given in greater detail below.

In a seventh embodiment, an example of which is shown in FIG. 1, the sports theme hands-free binocular glasses 10 include all the features of the first embodiment, and the overall shape of the ornamental device 40 is substantially the shape of a portion of a baseball. The first design element 45 may comprise, for example, an integrated or molded element in the shape of the threads of the baseball. The second design element 60 may comprise, for example, the color scheme of a particular baseball team, the name of a baseball player for the particular baseball team, and/or the number of the player.

Figure 2:
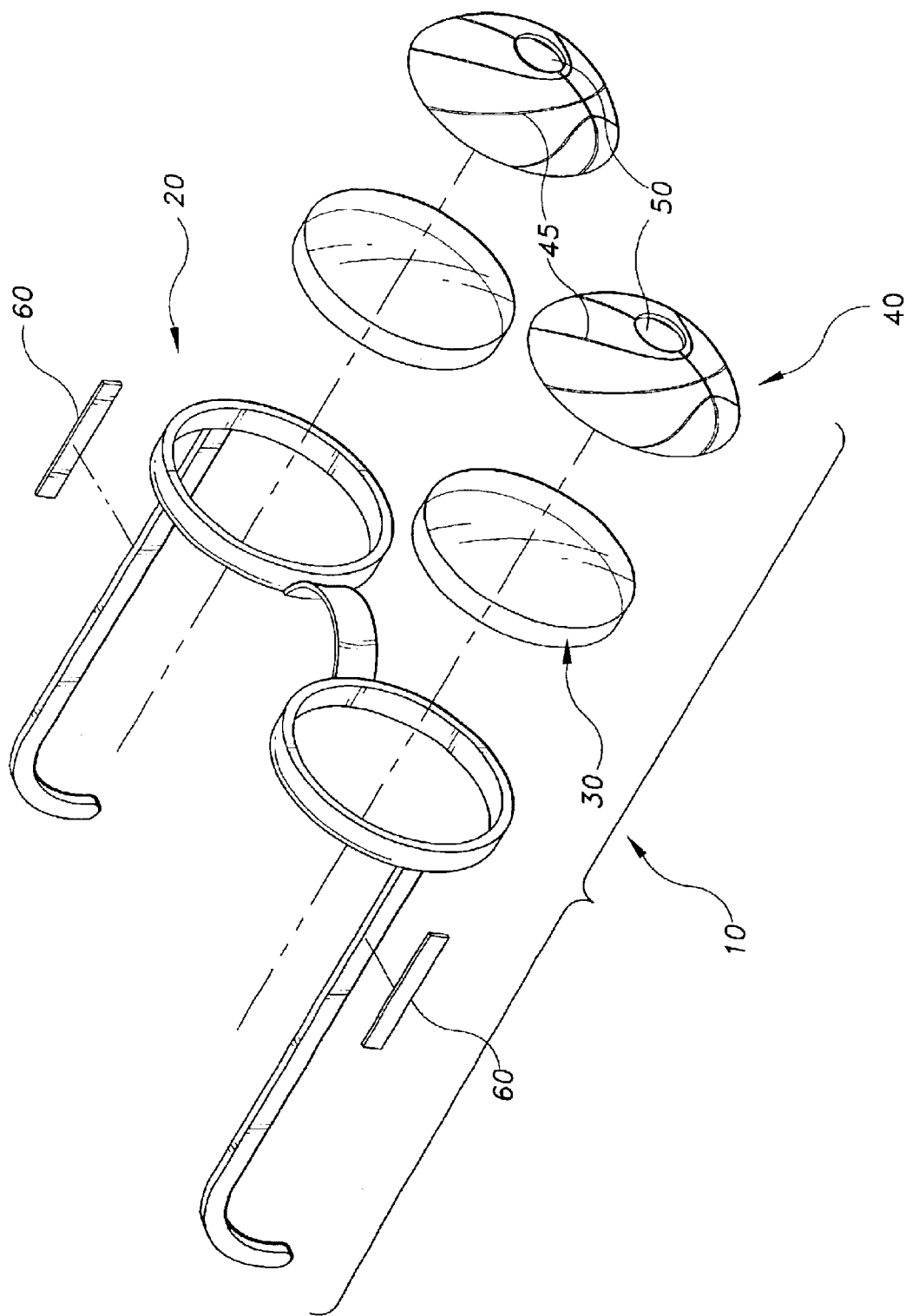
FIG. 2 is an environmental, perspective view of sports theme hands-free binocular glasses according to the present invention with a basketball theme.

In an eighth embodiment, an example of which is shown in FIG. 2, the sports theme hands-free binocular glasses 10 include all the features of the first embodiment, and the overall shape of the ornamental device 40 is substantially the shape of a portion of a basketball. The first design element 45 may comprise, for example, an integrated or molded element in the shape of the grooves of the basketball. The second design element 60 may comprise, for example, the color scheme of a particular basketball team, the name of a basketball player for the particular basketball team, and/or the number of the player.

Figure 4:
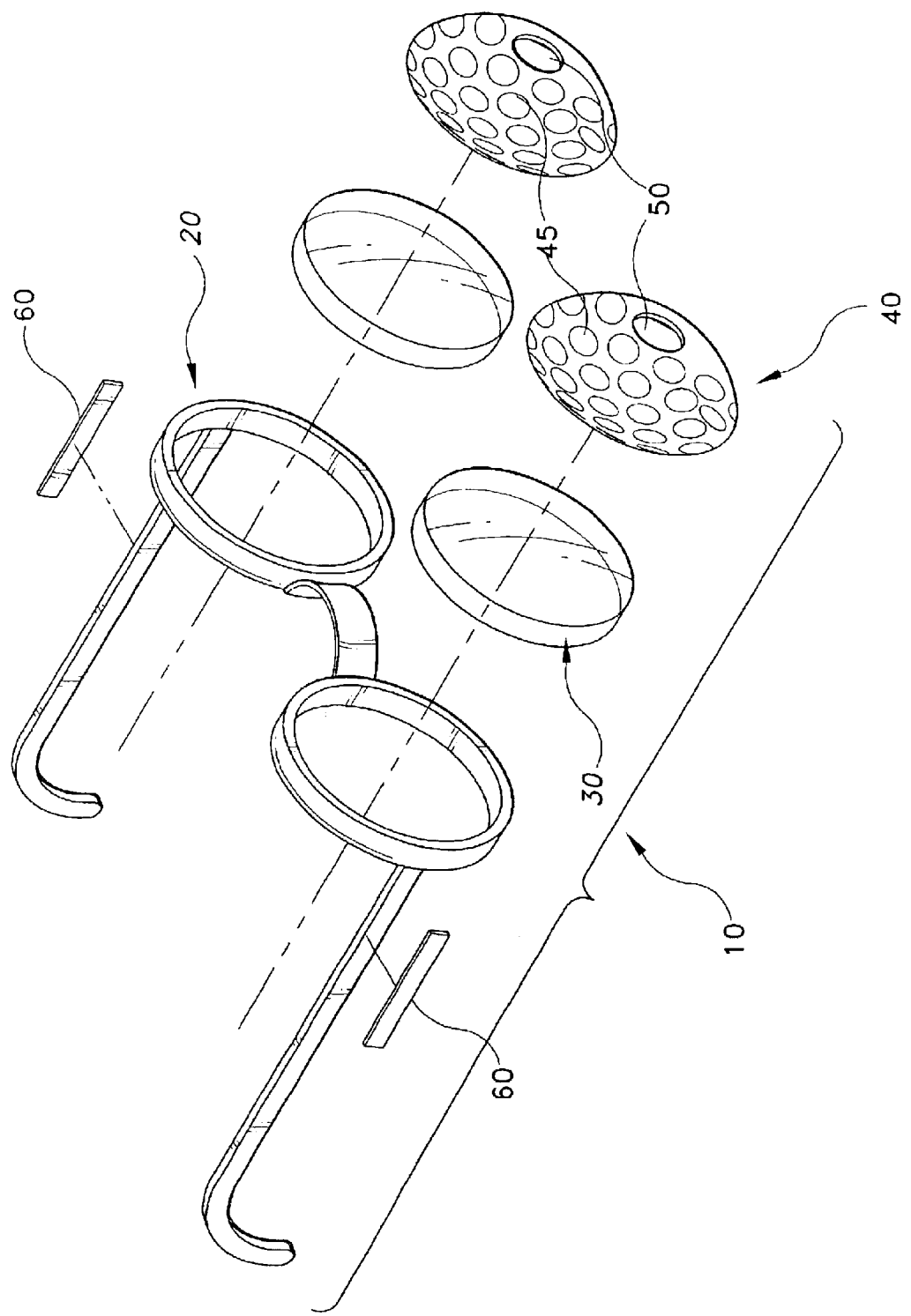
FIG. 4 is an environmental, perspective view of sports theme hands-free binocular glasses according to the present invention with a golf theme.

In a ninth embodiment, an example of which is shown in FIG. 4, the sports theme hands-free binocular glasses 10 include all the features of the first embodiment, and the overall shape of the ornamental device 40 is substantially the shape of a portion of a golf ball. The first design element 45 may comprise, for example, an integrated or molded element in the shape of the dimples of the golf ball. The second design element 60 may comprise, for example, the name of a golf player, and/or the name of a golf tournament.

In a tenth embodiment, an example of which is shown in FIG. 5, the sports theme hands-free binocular glasses 10 include all the features of the first embodiment, and the overall shape of the ornamental device 40 is substantially the shape of a hockey puck or a portion of a hockey puck. The first design element 45 may comprise, for example, a sticker bearing the name of a hockey team. The second design element 60 may comprise, for example, an applique in the shape of a team logo.

Figure 7:
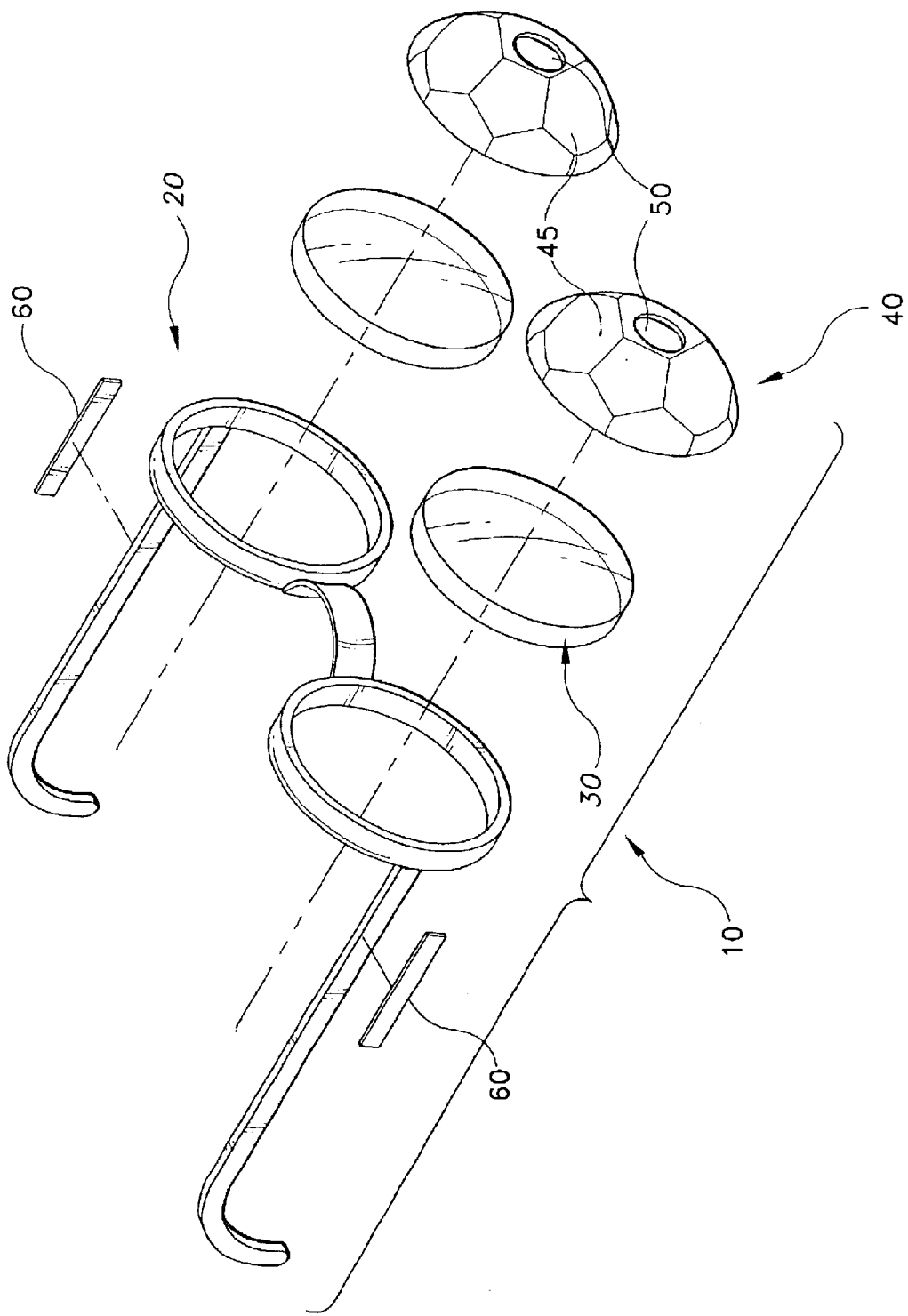
FIG. 7.is an environmental, perspective view of sports theme hands-free binocular glasses according to the present invention with a soccer theme.

In an eleventh embodiment, an example of which is shown in FIG. 7, the sports theme hands-free binocular glasses 10 include all the features of the first embodiment, and the overall shape of the ornamental device 40 is substantially the shape of a portion of a soccer ball. The first design element 45 may comprise, for example, an integrated or molded element in the shape of the panels of the soccer ball. The second design element 60 may comprise, for example, the color scheme of a particular soccer team, the name of a soccer player for the particular soccer team, and/or the number of the player.

Figure 8:
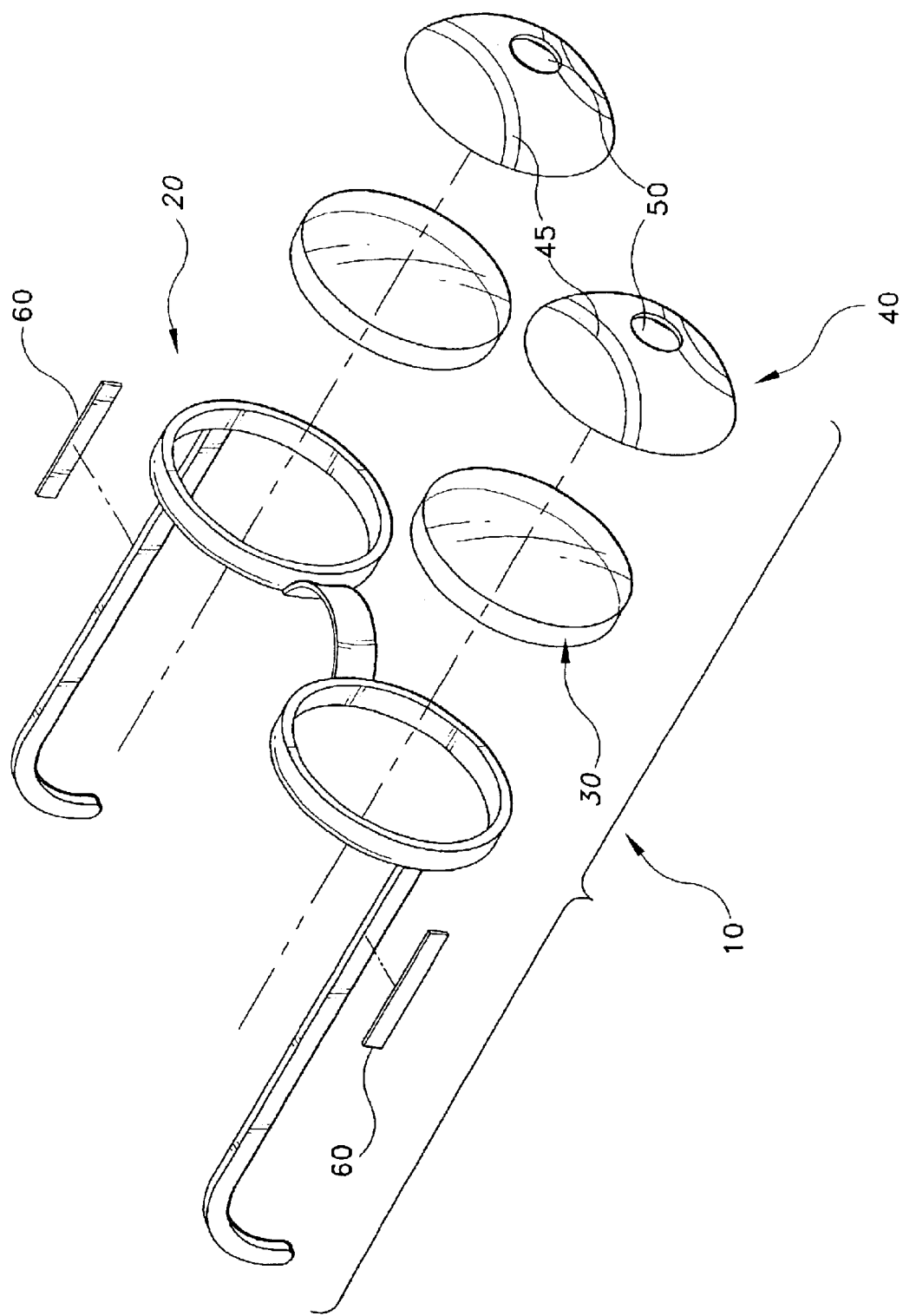
FIG. 8 is an environmental, perspective view of sports theme hands-free binocular glasses according to the present invention with a tennis theme.

In a twelfth embodiment, an example of which is shown in FIG. 8, the sports theme hands-free binocular glasses 10 include all the features of the first embodiment, and the overall shape of the ornamental device 40 is substantially the shape of a portion of a tennis ball. The first design element 45 may comprise, for example, an integrated or molded element in the shape of the grooves of the tennis ball. The second design element 60 may comprise, for example, the name of a tennis player.

In a thirteenth embodiment, examples of which are shown in FIGS. 1 to 8, the sports theme hands-free binocular glasses 10 include all the features of the first embodiment, and the eyeglass frame 20 comprises a second design element 60. The second design element 60 may comprise, for example, a sticker or an applique adapted for attachment to the surface of the eyeglass frame 20, or a design element integrated or molded into the overall shape of the eyeglass frame 20. The second design element 60 may comprise, for example, a color scheme for a team, a logo, a name, a number corresponding with a player, etc.

In a fourteenth embodiment, examples of which are shown in FIGS. 1 to 8, the sports theme hands-free binocular glasses 10 include all the features of the thirteenth embodiment, and the second design element 60 comprises a sports-related design element. The sports-related design element may comprise, for example, a sports-related sticker or a sports-related applique adapted for attachment to the surface of the eyeglass frame 20, or a sports-related design element integrated or molded into the overall shape of the eyeglass frame 20.

In a fifteenth embodiment, examples of which are shown in FIGS. 1 to 8, the sports theme hands-free binocular glasses 10 include all the features of the first embodiment, and the sports theme hands-free binocular glasses 10 further comprise a sports-related design element. The sports-related design element may comprise, for example, the first design element 45 or the second design element 60, either of which may comprise a sports-related sticker or a sports-related applique adapted for attachment to the surface of the sports theme hands-free binocular glasses 10, or a design element integrated or molded into the overall shape of the sports theme hands-free binocular glasses 10.

Figure 3:
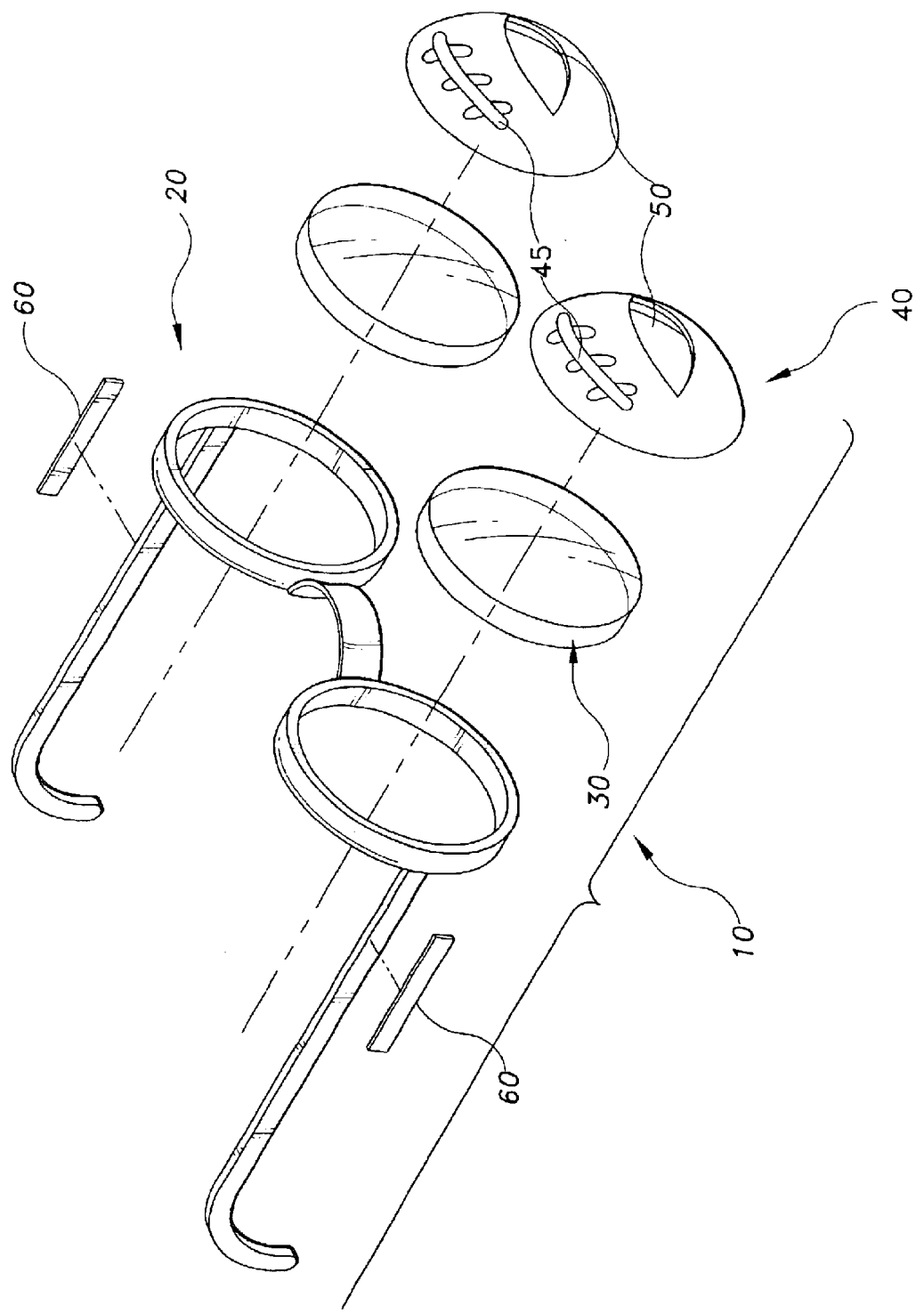
FIG. 3 is an environmental, perspective view of sports theme hands-free binocular glasses according to the present invention with a football theme.

In a sixteenth embodiment, examples of which are shown in FIG. 3, the sports theme hands-free binocular glasses 10 include all the features of the first embodiment, and the overall shape of the ornamental device 40 is substantially oblong. The substantially oblong shape is similar to that of the shape of a football. The sports theme hands-free binocular glasses 10 of the sixteenth embodiment may include a first design element 45. The first design element 45 may comprise, for example, an integrated or molded element in the shape of the threads of the football. The second design element 60 may comprise, for example, the color scheme and/or logo of a particular football team.

In a seventeenth embodiment, an example of which is shown in FIG. 3, the sports theme hands-free binocular glasses 10 include all the features of the first embodiment, and the opening 50 has a shape which is substantially the cross-section of a football. The sports theme hands-free binocular glasses 10 of the seventeenth embodiment may include a first design element 45. As with the sixteenth embodiment, the first design element 45 may comprise, for example, an integrated or molded element in the shape of the threads of the football. The second design element 60 may comprise, for example, the color scheme and/or logo of a particular football team.

In an eighteenth embodiment, examples of which are shown in FIGS. 1 to 8, the sports theme hands-free binocular glasses 10 include all the features of the first embodiment, and the ornamental device 40 comprises a material which is used to make the outer surface of a sports-related device. For example, the ornamental device 40 as shown in FIG. 1 could be made from leather, similar to that of a real baseball. Other materials, i.e. natural leather, manmade leather, pigskin, plastic, rubber, felt, etc., may comprise used as appropriate to further emulate the sports-related device being depicted by the ornamental device 40.

Figure 9:
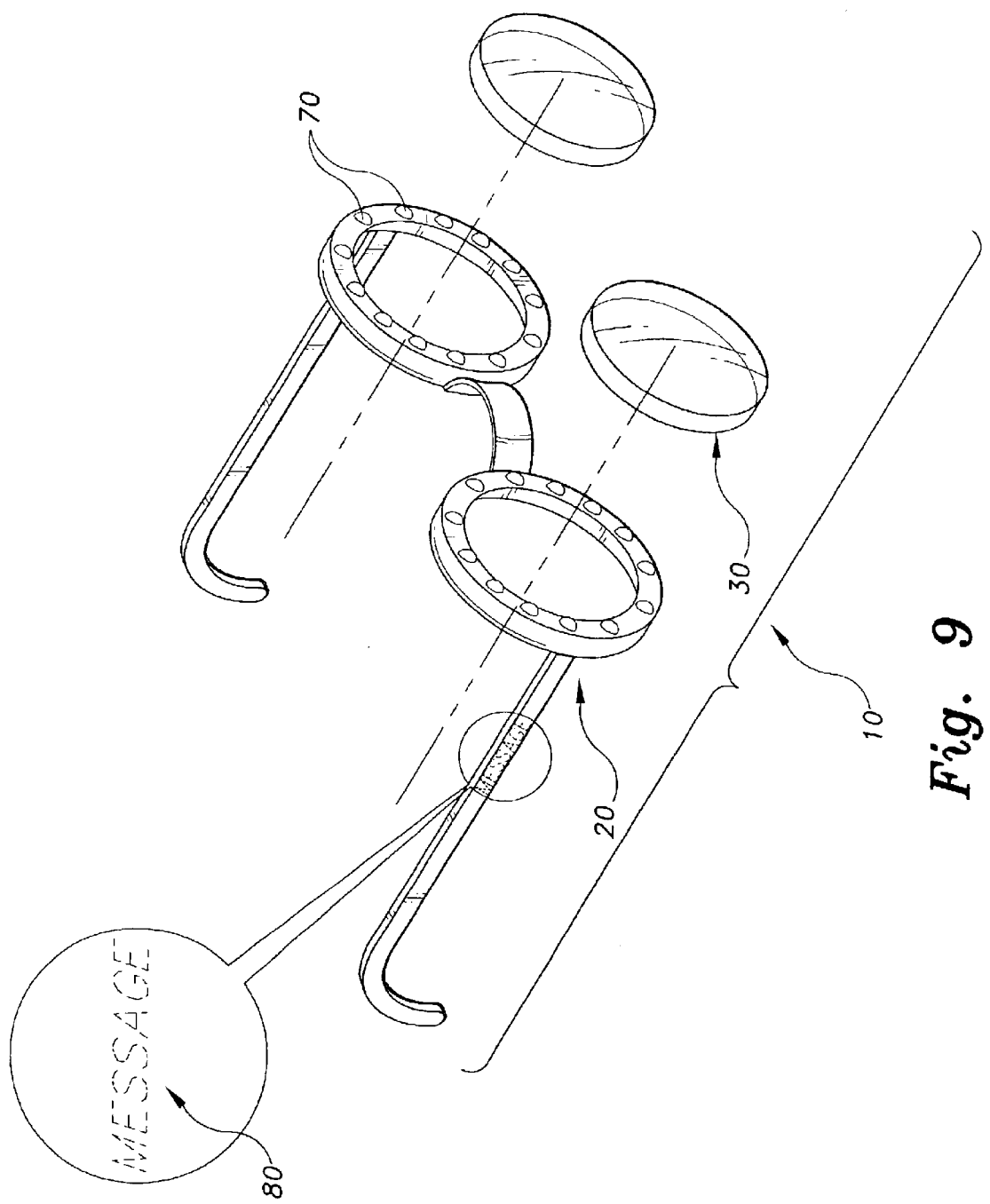
FIG. 9 is an environmental, perspective view of hands-free binocular glasses according to the present invention with decorative and design elements.

In a nineteenth embodiment, an example of which is shown in FIG. 9, binocular glasses 10 comprise an eyeglass frame 20, a binocular device 30 adapted for attachment to the eyeglass frame 20, a decorative element 70 adapted for attachment to the eyeglass frame 20, and a design element 80 adapted for attachment to the surface of the eyeglass frame 20, where the binocular glasses 10 are adapted for use as a hands-free device. The binocular glasses 10 as shown in FIG. 9 are an elegant version of the present invention which are more appropriate for concerts, operas and events where the wearer might be more fashion-conscious.

The decorative element 70 may comprise, for example, gold beads or cubic zirconium gems, adapted for attachment to the eyeglass frame 20 to add to the aesthetic appeal of the binocular glasses 10.

The design element 80 may comprise, for example, a sticker or an applique bearing a printed message, or a design element integrated or molded into the surface of the eyeglass frame 20 and forming a recognizable message. The design element 80 may comprise flocking material. The design element 80 may form a message by selectively attaching a flocking material to the surface of the eyeglass frame 20 thus forming recognizable letters. The flocking material may be any suitable flocking material, such as natural or synthetic fur, natural or synthetic feathers, felt and the like.

In a twentieth embodiment, examples of which are shown in FIGS. 1 to 8, sports theme hands-free binocular glasses 10 comprise an eyeglass frame 20, a binocular device 30 adapted for attachment to the eyeglass frame 20, an ornamental device 40 adapted for attachment to the eyeglass frame 20, and a sports-related design element, where the ornamental device 40 has an overall shape, where the overall shape of the ornamental device 40 is substantially the shape of a sports-related device, where the ornamental device 40 has an opening 50 which allows light to pass through the opening 50 and into the binocular device 30, where the ornamental device 40 comprises a first design element 45, where the first design element 45 has a first design element shape which is substantially the shape of an attribute of the sports-related device, and where the sports theme hands-free binocular glasses 10 are adapted for use as a hands-free device.

It is to be understood that the present invention is not limited to the embodiments described above, but encompasses any and all embodiments within the scope of the following claims.

I claim:

1. Sports theme hands-free binocular glasses comprising:
    an eyeglass frame;
    a binocular device adapted for attachment to the eyeglass frame;
    an ornamental device adapted for attachment to the eyeglass frame;
    wherein the ornamental device has an overall shape;
    wherein the overall shape of the ornamental device is a sports-related ornament and is substantially the shape of a specific sports device which the ornament represents; and
    wherein the ornamental device has an opening which allows light to pass through the opening and into the binocular device.

2. The sports theme hands-free binocular glasses of claim 1, wherein the overall shape of the ornamental device is substantially semispherical.

3. The sports theme hands-free binocular glasses of claim 1, wherein the overall shape of the ornamental device is substantially cylindrical.

4. The sports theme hands-free binocular glasses of claim 1, wherein the ornamental device is hollow and adapted to enclose the binocular device.

5. The sports theme hands-free binocular glasses of claim 1, wherein the ornamental device comprises a first design element.

6. The sports theme hands-free binocular glasses of claim 5, wherein the first design element has a first design element shape which is substantially the shape of an attribute of the sports-related device.

7. The sports theme hands-free binocular glasses of claim 1, wherein the overall shape of the ornamental device is substantially the shape of a portion of a baseball.

8. The sports theme hands-free binocular glasses of claim 1, wherein the overall shape of the ornamental device is substantially the shape of a portion of a basketball.

9. The sports theme hands-free binocular glasses of claim 1, wherein the overall shape of the ornamental device is substantially the shape of a portion of a golf ball.

10. The sports theme hands-free binocular glasses of claim 1, wherein the overall shape of the ornamental device is substantially the shape of a hockey puck or a portion of a hockey puck.

11. The sports theme hands-free binocular glasses of claim 1, wherein the overall shape of the ornamental device is substantially the shape of a portion of a soccer ball.

12. The sports theme hands-free binocular glasses of claim 1, wherein the overall shape of the ornamental device is substantially the shape of a portion of a tennis ball.

13. The sports theme hands-free binocular glasses of claim 5, wherein the eyeglass frame comprises a second design element.

14. The sports theme hands-free binocular glasses of claim 13, wherein the second design element comprises a sports-related design element.

15. The sports theme hands-free binocular glasses of claim 1, wherein the sports theme hands-free binocular glasses further comprise a sports-related design element.

16. The sports theme hands-free binocular glasses of claim 1, wherein the overall shape of the ornamental device is substantially oblong.

17. The sports theme hands-free binocular glasses of claim 1, wherein the opening has a shape which is substantially the cross-section of a football.

18. The sports theme hands-free binocular glasses of claim 1, wherein the ornamental device comprises a material which is used to make the outer surface of a sports-related device.

19. Sports theme hands-free binocular glasses comprising:

an eyeglass frame;

a binocular device adapted for attachment to the eyeglass frame;

an ornamental device adapted for attachment to the eyeglass frame; and a sports-related design element;

wherein the ornamental device has an overall shape;

wherein the overall shape of the ornamental device is a sports-related ornament and is substantially the shape of the sports-related design element which the ornament represents;

wherein the ornamental device has an opening which allows light to pass through the opening and into the binocular device;

wherein the ornamental device comprises a first design element; and wherein the first design element has a first design element shape which is substantially the shape of an attribute of the sports-related design element.

* * * * *